United States Patent
Estes et al.

(10) Patent No.: US 7,287,903 B2
(45) Date of Patent: Oct. 30, 2007

(54) METHOD AND APPARATUS FOR RAPID THERMAL TESTING

(75) Inventors: Timothy A. Estes, Albuquerque, NM (US); Robert Neves, Anaheim, CA (US)

(73) Assignee: Conductor Analysis Technologies, Inc., Albuquerque, NM (US)

( * ) Notice: Subject to any disclaimer, the term of this patent is extended or adjusted under 35 U.S.C. 154(b) by 0 days.

(21) Appl. No.: 10/783,166

(22) Filed: Feb. 20, 2004

(65) Prior Publication Data

US 2004/0233966 A1 Nov. 25, 2004

Related U.S. Application Data

(60) Provisional application No. 60/449,276, filed on Feb. 20, 2003.

(51) Int. Cl.
*G01N 25/00* (2006.01)
*G01R 31/00* (2006.01)

(52) U.S. Cl. .................. 374/11; 374/57; 324/760; 702/118

(58) Field of Classification Search .............. 374/50, 374/57, 33, 12, 11; 324/760, 158.1, 763, 324/538
See application file for complete search history.

(56) References Cited

U.S. PATENT DOCUMENTS

| | | | | |
|---|---|---|---|---|
| 4,367,961 A | * | 1/1983 | Griffin | .................. 374/46 |
| 4,517,512 A | * | 5/1985 | Petrich et al. | .............. 714/724 |
| 4,871,965 A | * | 10/1989 | Elbert et al. | ................. 324/760 |
| 5,324,481 A | * | 6/1994 | Dunn et al. | .................... 422/64 |
| 5,337,893 A | * | 8/1994 | Nami et al. | ................. 206/722 |
| 5,392,219 A | | 2/1995 | Birch et al. | |
| 5,451,885 A | | 9/1995 | Birch et al. | |
| 5,506,510 A | * | 4/1996 | Blumenau | .................... 324/754 |
| 5,701,667 A | | 12/1997 | Birch et al. | |
| 5,834,946 A | * | 11/1998 | Albrow et al. | .............. 324/760 |
| 5,942,432 A | * | 8/1999 | Smith et al. | ............. 435/303.1 |
| 5,986,447 A | * | 11/1999 | Hanners et al. | .......... 324/158.1 |
| 6,040,691 A | * | 3/2000 | Hanners et al. | .......... 324/158.1 |
| 6,304,093 B1 | * | 10/2001 | Hilmoe et al. | .............. 324/760 |
| 6,406,918 B1 | * | 6/2002 | Bannister et al. | ........... 436/155 |

(Continued)

*Primary Examiner*—Gail Verbitsky
(74) *Attorney, Agent, or Firm*—Jeffrey D. Myers; Philip D. Askenazy; Peacock Myers, P.C.

(57) ABSTRACT

An apparatus for rapid thermal testing of samples consisting of a single sample chamber in which the samples are preferably arranged circularly around the opening through which a fluid of varying temperature, preferably air, is introduced to provide for rapid, uniform cooling and heating of the samples. The samples are preferably uniformly spaced to allow for uniform air flow. The samples are mounted in slots which are preferably oriented radially outward from the opening. The sample mounts comprise electrical connectors which form a network connected to at least one ohmmeter for measuring the resistance of the samples. The samples preferably comprise test coupons, each with multiple daisy-chained nets of vias or other components to be tested. Also a method for thermal testing of samples consisting of steps to characterize the samples before the test is run. First, the resistance of the samples which correlates to each target temperature is determined, and the time required for the samples to reach that resistance when they are heated or cooled is measured. Then, for reliability testing, the temperature of the samples is cycled between the target temperatures, where the cycle segment durations are given by the times measured in the characterization steps.

36 Claims, 4 Drawing Sheets

U.S. PATENT DOCUMENTS

| | | | |
|---|---|---|---|
| 6,472,156 B1 * | 10/2002 | Wittwer et al. | 435/6 |
| 6,787,338 B2 * | 9/2004 | Wittwer et al. | 435/91.2 |
| 7,084,659 B2 * | 8/2006 | Delucco et al. | 324/765 |
| 2003/0122566 A1 * | 7/2003 | Takahashi et al. | 324/760 |
| 2003/0231693 A1 * | 12/2003 | Hutter | 374/12 |
| 2005/0194989 A1 * | 9/2005 | Delucco et al. | 324/765 |

* cited by examiner 1.0 x 0.5 inch Coupon 1.0 x 1.0 inch Coupon 2.0 x 1.0 inch Coupon

METHOD AND APPARATUS FOR RAPID THERMAL TESTING

CROSS-REFERENCE TO RELATED APPLICATIONS

This application claims the benefit of the filing of U.S. Provisional Patent Application Ser. No. 60/449,276, entitled "Highly Accelerated Thermal Shock", filed on Feb. 20, 2003, the specification of which is incorporated herein by reference.

BACKGROUND OF THE INVENTION

1. Field of the Invention (Technical Field)

The present invention relates to a method and apparatus for thermal shock reliability testing of electronic components such as printed circuit boards and solder joints. The present invention provides for testing the thermal reliability of devices in a time period which is up to ten times shorter than currently used tests.

2. Background Art

Note that the following discussion is given for more complete background of the scientific principles and is not to be construed as an admission that such concepts or publications listed are prior art for patentability determination purposes.

Thermal shock testing has long been the accepted method to check the reliability of plated-through holes and solder joint connections in electronic components. The first standard was MIL-STD-202 Method 107, which originated in the late 1950's and was last updated in 1984. For printed circuit boards and solder joints, the acceleration mechanism for reliability is a function of the thermal coefficient of expansion of the materials used in the device under test (DUT). Along with the difference between the temperature extremes of the test environment, this coefficient determines the stresses introduced in the DUT and the reliability acceleration that is exhibited.

Thermal shock conditions are produced by rapidly moving the DUT between two temperature extremes, and typically require that the transition time between the extremes is less than five minutes, thereby creating a shock condition. Ordinarily the DUT has a "coupon" incorporated into it, or alternatively, a standalone test coupon is used, and the electrical characteristics, such as resistance, of the coupon are monitored. The coupon comprises standard components, such as vias, in a variety of layouts, and its connections to the test system are determined by the particular system. Thus it is actually the coupon, and not the DUT, that is tested. Because the coupon is manufactured by same process and (optionally) at the same time as the DUT, the reliability of the coupon is an excellent indication of the reliability of the DUT.

Typical values for the lower temperature extreme range from −40° C. to −65° C., while the upper temperature extreme typically ranges from 85° C. to 200° C. The time the DUT must remain at a temperature extreme before reaching equilibrium, or dwell time, can vary from a few minutes to an hour, depending on the method of producing the temperature extremes, the capacity for heat transmission, and the mass of the DUT. For massive parts over 136 kg, dwell times can reach eight hours. This time is required because typical test methods do not measure the temperature of the DUT samples directly, and so an estimate of the time required for the DUT to come to equilibrium at the desired temperature is required. Considering that the number of cycles for a complete test can range from hundreds to thousands of cycles, this equilibrium time is very significant.

Historically, the two most used methodologies for producing thermal shock environments are air-to-air and liquid-to-liquid. Air-to-air thermal shock systems utilize two separate chambers, each set to the opposite temperature extreme, and a mechanism to move the DUT between the two chambers. While these chambers are readily available, they are expensive to operate and provide a low heat exchange rate to the DUT. Dual liquid-to-liquid chambers, each controlled to the opposite temperature extreme, utilize special liquids, and a mechanism to move the DUT between the two liquids. Unlike the air-to-air chambers, this very expensive liquid provides an excellent heat exchange rate, and thus, is able to move the DUT rapidly between temperatures extremes. Since both these methods physically move the DUT, the cabling to the DUT must be capable of moving.

Reliability of the DUT is determined by monitoring the resistance of the samples during the test. As samples fail, the resistance changes, thus providing reliability data. For the above testing systems, which require transportation of the samples, it is very difficult to make electrical measurements during cycling, and the cabling is typically of lengths that do not allow for high accuracy measurements and limits the number of data points that can be monitored. The resultant infrequent monitoring also makes detection of glitch conditions, and even the actual failure point, marginal at best.

Another thermal shock system is the Interconnect Stress Testing (IST) system disclosed in U.S. Pat. Nos. 5,392,219, 5,451,885, and 5,701,667 to Birch et al. This method uses the copper circuits (both traces and vias) integrated into the DUT as resistance heating elements, and is cooled to ambient temperature with circulated air. This method has the advantage of predetermining the amount of current that raises the samples to the desired temperature. This eliminates the need for dwell time when the actual testing is carried out. There are a number of drawbacks to this technique, however. The current required to heat the samples to a desired temperature is not empirically determined; rather, it is calculated from the resistance of the sample at room temperature. In addition, as samples fail during the test, the resistance of the system changes, thus requiring the applied current to be modified in order to maintain the desired temperature. Unfortunately the appropriate new value of the current is difficult if not impossible to determine, resulting in poor control. For example, the upper temperature may exceed a required maximum temperature for a given DUT, such as that determined by the glass transition temperature $T_g$ of certain materials used in the coupon or DUT. In addition, the method does not include the cold portion of the thermal cycle, so it can not replicate traditional thermal shock tests, both in low temperature extension and overall temperature range.

Accordingly there is a need for a thermal shock testing system that provides for exact determination of the sample temperature so the dwell time can be eliminated, temperature monitoring without the use of the electrical characteristics of the samples, continuous sample monitoring, and a temperature cycle with temperature extremes both above and below ambient temperature without requiring the samples to be moved.

SUMMARY OF THE INVENTION
(DISCLOSURE OF THE INVENTION)

The present invention is of an apparatus for thermal testing of one or more samples, said apparatus comprising a single sample chamber, a cooler and a heater to vary the temperature of a fluid, an opening in the chamber for introduction of the fluid, and a plurality of sample mounts for receiving the samples circularly arranged around the opening, wherein the fluid varies temperature of the one or more samples. The temperature preferably ranges from being lower than the ambient temperature to higher than the ambient temperature. The fluid preferably comprises compressed dry air which is preferably cooled to a temperature lower than the lowest desired temperature and is subsequently heated to the various desired temperatures.

The sample mounts preferably are evenly spaced so that sufficient space exists between the samples to permit uniform flow of the fluid. The sample mounts preferably comprise slots which are oriented radially outward from said opening. The sample mounts also preferably comprise electrical connectors which comprise an electronic switching network which comprises at least one precision ohmmeter. The network is preferably in communication with a computer or processor which preferably comprises a data acquisition system. The samples preferably comprise test coupons comprising at least one net, where a net comprises a daisy-chain of vias or other components to be tested.

The present invention is also a method of performing thermal testing of one or more samples comprising the steps of stabilizing the samples at a first desired temperature and measuring a first resistance of the samples once stabilized, stabilizing the samples at a second desired temperature and measuring a second resistance of the samples once stabilized, determining a first duration starting from the second resistance for the samples to reach the first resistance, determining a second duration starting from the first resistance for the samples to reach the second resistance; and subjecting the samples to a plurality of temperature cycles, the number of cycles being preferably predetermined, ranging between the first desired temperature and the second desired temperature, wherein a temperature of the samples is changed for the first duration in order for them to reach the first desired temperature and the temperature of the samples is changed for the second duration in order for them to reach the second desired temperature. Preferably the stabilizing steps are performed before the determining steps. Preferably the method includes determining a number of the samples which have failed after the predetermined number of cycles have been performed, or alternatively, monitoring the number of the samples which have failed during the subjecting step. The invention is further of a thermal shock test performed according this method.

The present invention is also of a method of thermally testing one or more samples comprising the steps of varying the temperature of the samples until the temperature is stabilized at a desired temperature and measuring a stabilized resistance of the samples at the desired temperature, determining the duration for the samples to reach the stabilized resistance correlated with the desired temperature, and changing the temperature of the one or more samples for the duration so that they reach the desired temperature. Preferably the determining step is performed for each of at least two desired temperatures after the varying step is performed for those least two desired temperatures. The duration to reach a stabilized resistance correlated with a desired temperature is preferably measured from when a resistance of the samples has a value correlated with a different desired temperature, and the changing step is preferably repeated alternating between each of the at least two desired temperatures. The determining step is preferably repeated until at least two measurements of the time for the samples to reach the stabilized resistance correlated with the desired temperature are within a predetermined error interval. The determining step is preferably repeated until at least two measurements of the stabilized resistance for the desired temperature are within a predetermined error interval. The invention is further of a thermal shock test performed according to this method.

Objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

DESCRIPTION OF THE PREFERRED EMBODIMENTS (BEST MODES FOR CARRYING OUT THE INVENTION)

The present invention is of a method and apparatus, preferably referred to as Highly Accelerated Thermal Shock (HATS), for rapidly accelerating the thermal testing, including thermal shock testing, of devices, including but not limited to electronic components. By reducing the time to determine reliability of such devices by up to a factor of ten, development costs and time-to-market are dramatically reduced. In addition, the apparatus of the present invention is much less expensive than most commonly used thermal shock testing equipment.

As used throughout the specification and claims, "device under test", "DUT", or "sample" means any device, electronic component, printed circuit board (PCB), printed wiring board (PWB), plated through hole (PTH) interconnect, net, via, solder joint, coupon, and the like, or any other item or component thereof which is to be tested for thermal reliability.

As used throughout the specification and claims, "fluid" means liquid, vapor, air, gas, inert gas, and the like.

Figure 1:
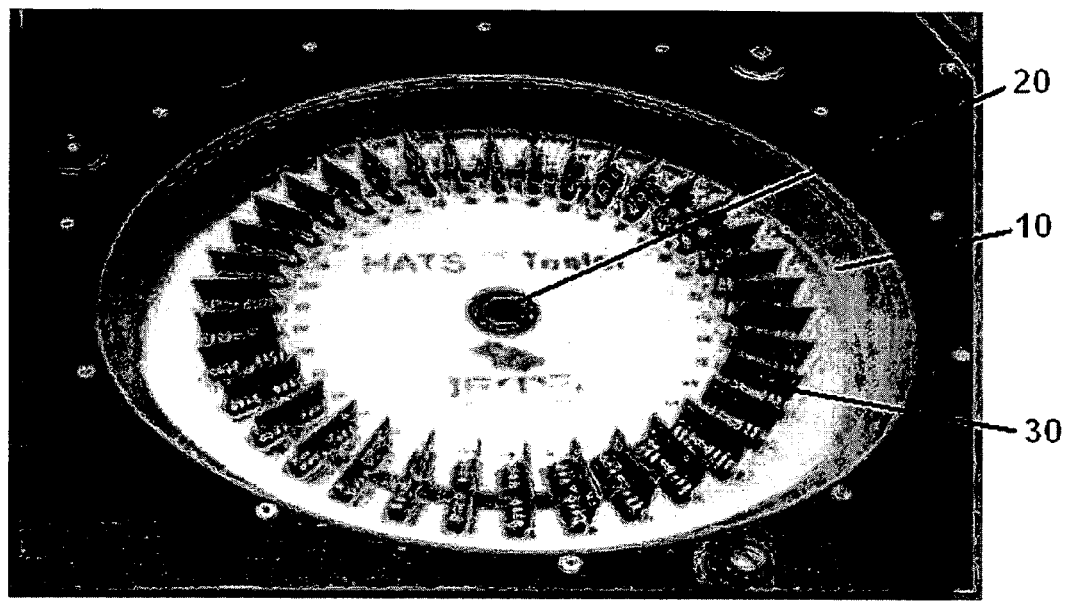
FIG. 1 is a view of a preferred sample layout for the apparatus of the present invention.

In order to rapidly cycle the temperature across the desired temperature range it is important to configure the samples in the apparatus so that the flow of cooling or heating fluid is both unimpeded and uniform across all the samples. FIG. 1 depicts sample chamber 10 of a preferred embodiment of the present invention. There is a single opening 20 in the chamber through which the cooling or heating fluid, preferably air, is introduced. The air is preferably dried by a drier to remove moisture, and is then compressed, preferably by a two-stage compressor. The compressed dry air is then preferably cooled to approximately −90° C. and then heated by a high power heater to whatever target temperature the test requires at any moment. Optionally, the air may be cooled exactly to target temperatures which are below ambient temperature, and separately heated exactly to target temperatures which are above ambient temperature. Any means for cooling or heating the fluid may be used.

Figure 2:
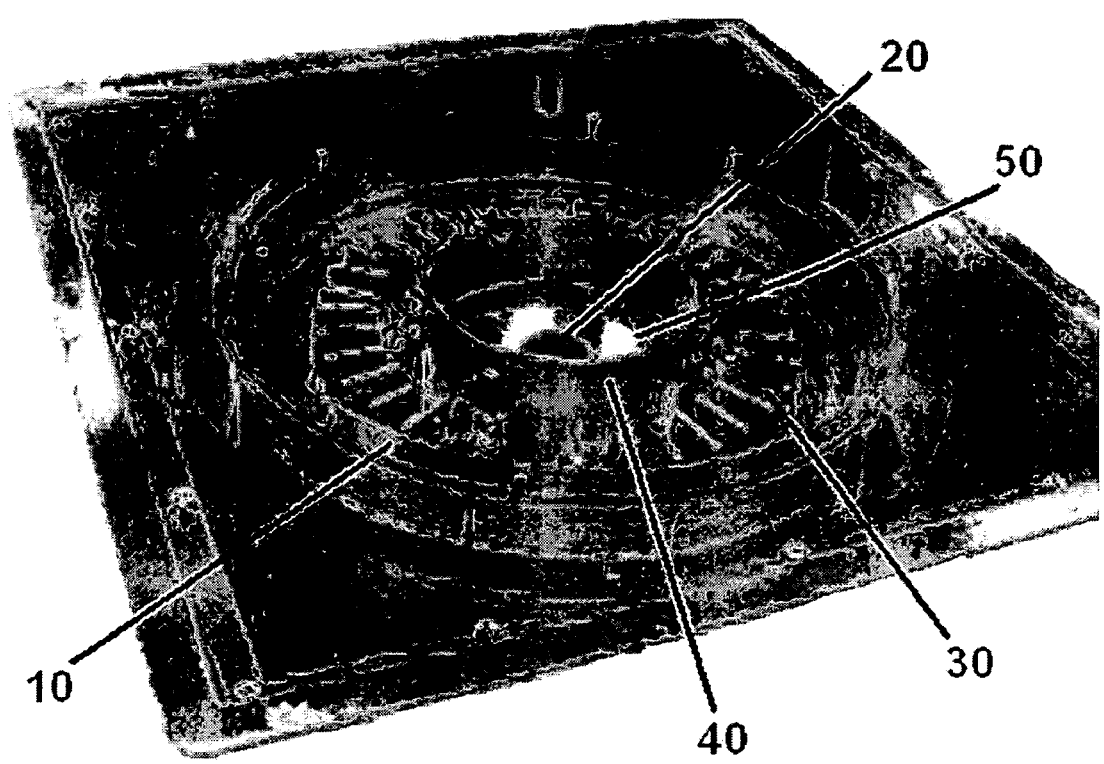
FIG. 2 is another view of the sample layout depicting an optional flow distributor.

Samples 30 are retained in sample mounts and preferably arranged circumferentially about opening 20. Preferably samples 30 are evenly spaced, and are all an equal distance from opening 20. The DUTs pictured in FIGS. 1 and 2 comprise circuit boards. For such DUTs, or others that are similar in shape, it is important that the orientation of the samples with respect to the opening is such that the fluid flow is unimpeded. In the preferred embodiment an edge of the aforesaid board is mounted in sample chamber 10 with an outward radial orientation with respect to the fluid opening. The combination of this orientation and the even spacing ensures that all samples are cooled or heated equally and as rapidly as possible while maximizing the number of samples which can be accommodated in sample chamber 10, and enables the use of a single chamber for both heating and cooling.

Optionally, uniform cooling and heating of all samples is further enhanced by the use of an air distribution system. In one embodiment the air distribution is performed by perforated barrier 40, depicted in FIG. 2, which surrounds opening 20 and is situated between opening 20 and samples 30. Once sample chamber 10 is closed, the lid of the unit contacts barrier 40, forming pressure chamber 50 within sample chamber 10. As fluid is introduced through opening 20, it first fills pressure chamber 50, and then the fluid flows evenly in all directions out of pressure chamber 50 through the perforations in barrier 40, and toward samples 30. Although barrier 40 preferably comprises perforated metal, any material may be utilized which is sufficiently porous to not significantly impede airflow, while at the same time is able to maintain a slight overpressure in pressure chamber 50.

The sample mounts preferably comprise electrical contacts, which are used to electrically connect the samples to devices for measuring their electrical characteristics. Preferably the resistance of each sample, or multiple samples within each coupon, is measured by a precision ohmmeter or equivalent device, preferably operating in four-wire (Kelvin) mode, and the results are preferably communicated to a computer or processor for data acquisition and analysis. For the present invention, test coupons made according to the same process that will be used to manufacture the final parts are tested. These coupons incorporate electronic subcomponents, such as vias, which are subject to failure due to thermal cycling in the field.

Figure 3:
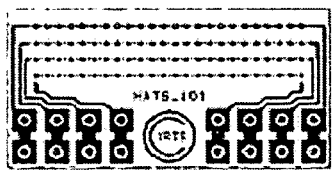
FIG. 3 shows examples of via daisy-chain test patterns on various test coupons.
Figure 3:
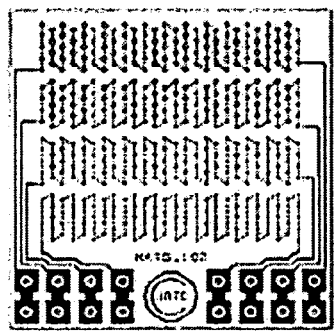
Figure 3:
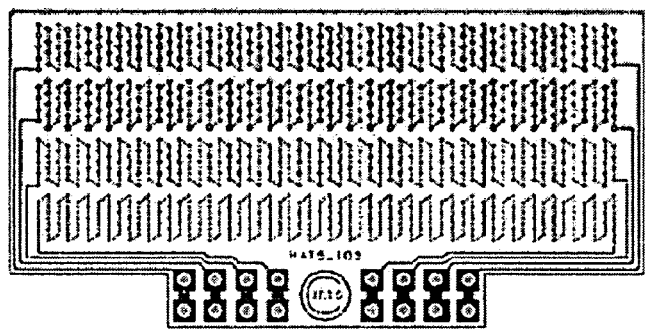

The particular coupons used are highly customizable depending on the user's needs. Test coupons that are used to study reliability of printed circuit boards, such as those shown in FIG. 3, typically range in size from one-half inch by one inch to one inch by two inches, but may be smaller or larger, and may contain 80 or more conductive layers. Each coupon contains a plurality of daisy-chain via nets, preferably four, that interconnect two or more layers in the coupon. Any number of layers may be accommodated. An advantage to having multiple nets per coupon is that more data can be collected for test run; the number of samples is not the number of coupons, but rather the total number of nets. Each net comprises a separate circuit and includes characteristics including but not limited to via type (through, blind, buried, or stacked), via diameter, land diameter, trace width, grid size, and interconnect sequence that mimic the structure to be evaluated. Further, the coupon may include or exclude characteristics such as teardrops, non-functional lands, soldermask coverage, and ground planes.

Any type of test coupon, whether standalone or integrated into a DUT, may be used according to the present invention. For example, test coupons that are used to study solder joints may include a plurality of chip packages or similar devices attached to one or both surfaces of the printed circuit board. The connections through the circuit board and chip package form a daisy-chain of solder joints connections. The condition of the solder joints is monitored by the precision electrical resistance of each daisy-chain net.

Thermal shock testing comprises rapidly cycling the DUTs from a minimum temperature to a maximum temperature and back again. If the cycle isn't long enough, the components within the DUT will not reach equilibrium at the desired temperature extreme, thus the desired change in temperature $\Delta T$ will not have been achieved. On the other hand, if the cycle is long enough to conservatively estimate that the DUTs have stabilized at the required temperature extreme, the test duration is undesirably long. Thus, in order to minimize the cycle time while providing the correct $\Delta T$ it is important to know that the temperature of the DUTs has reached either extreme. As the DUTs are tested during temperature cycling, the measured resistance of each net changes as various components, such as vias, fail. Thus it is important not to base cycle parameters on electrical characteristics of the samples while they are being tested.

The present invention is a novel method of characterizing the DUTs before actual testing so that the user can be assured that the samples reach the desired temperature extremes during testing. There is preferably a first characterization cycle, called the Reference Cycle, which preferably comprises the following steps. First, using the heating and/or cooling fluids the chamber temperature is set to one of the target temperatures as specified for the test and a thermocouple or the equivalent is used to verify that the chamber is at the target temperature. Next, the test samples are allowed to stabilize at the target temperature. Because it is well known that the sample resistance varies with changing temperature, the resistance will stabilize once the samples have stabilized at the target temperature. The resistance of feedback circuits, or the nets, integrated on or into the coupons or DUTs is what is actually measured. The final resistance, which is now correlated with that particular target temperature, is recorded. Optionally, the elapsed time, starting at one target temperature, to reach the stabilization resistance at another target temperature is also recorded. An advantage of this measurement is that it is conservative, in that as long as any of the samples has not reached the target temperature, the resistance will continue to change. Thus, a constant value of the resistance indicates that all of the samples are at the target temperature. These steps are optionally repeated until at least two resistance values which are within a predetermined error interval are recorded.

The Reference Cycle is then preferably performed for other target temperatures which are to be used in the test. Although there are preferably two target temperatures, a minimum and maximum, for a given test, this method can be utilized to perform thermal tests with any number of target temperatures.

After the Reference Cycles are completed, additional pretesting cycles are preferably performed. These cycles, called Timing Cycles, consist of raising or lowering the temperature of the test chamber between the desired target temperatures and measuring the time it takes for the resistance of the samples to reach the value determined in the Reference Cycles which correlates to that particular target temperature. Optionally, fluid that is at a temperature higher than the maximum target temperature, or lower than the minimum target temperature, may be used in the Timing Cycles in order to shorten the Test Cycle time even further. A number of Timing Cycles between the temperature extremes (which are equivalent to the desired Test Cycles) are preferably repeated until at least two time measurements for each target temperature agree within a predetermined error interval. Running the Timing Cycles is optional if the parameters during the Reference Cycles are equivalent to those that will be used for the Testing Cycles.

The purpose of these characterization cycles is that the actual testing can subsequently be performed without any reliance on electrical characteristics or measurements. This is important because the electrical properties, for example resistance, of the samples will change during the test as various components fail. The actual Test Cycles of the present invention are preferably performed according the timing information determined in the Timing Cycles, or optionally alternatively the elapsed time to reach the stabilization resistance recorded during the Reference Cycles. Optionally, fluid that is at a temperature higher than the maximum target temperature, or lower than the minimum target temperature, may be used in the Test Cycles to more rapidly heat or cool the sample to the desired temperature, thereby shortening the cycle time even more (as long as the same temperature fluids were used in the Timing Cycles). If desired by the user, an optional dwell time at each target temperature may be incorporated into the Test Cycle.

The present invention has further advantages as well. Because the characterization cycles are performed on the actual samples to be tested, the parameters of each test are optimized for the actual parts that are to be tested. In addition, because the exact time for the samples to reach the target temperature has previously been measured, there is no need, as in the prior art, to hold the samples for an estimated time to ensure they reach that temperature. Thus the cycle time is drastically reduced, and the testing can be completed up to ten times faster than existing methods. Finally, because the samples are stationary and do not have to be moved from one chamber to another, it is much easier to electrically connect them to the monitoring devices, and continuous monitoring is possible, eliminating the possibility of missing a failure point.

A preferred embodiment of the present invention is more specifically described in the following non-limiting example.

EXAMPLE

The example embodiment of the HATS system of the present invention was compared to two other systems: a Delphi two chamber air-to-air Thermal Shock system and an IST system. The HATS system has a temperature range of −60° C. to +160° C., with an air transition time between the two extremes of only thirty seconds. The system can accommodate 36 coupons, each with four independent nets, or circuits, providing 144 samples per test run.

Figure 4:
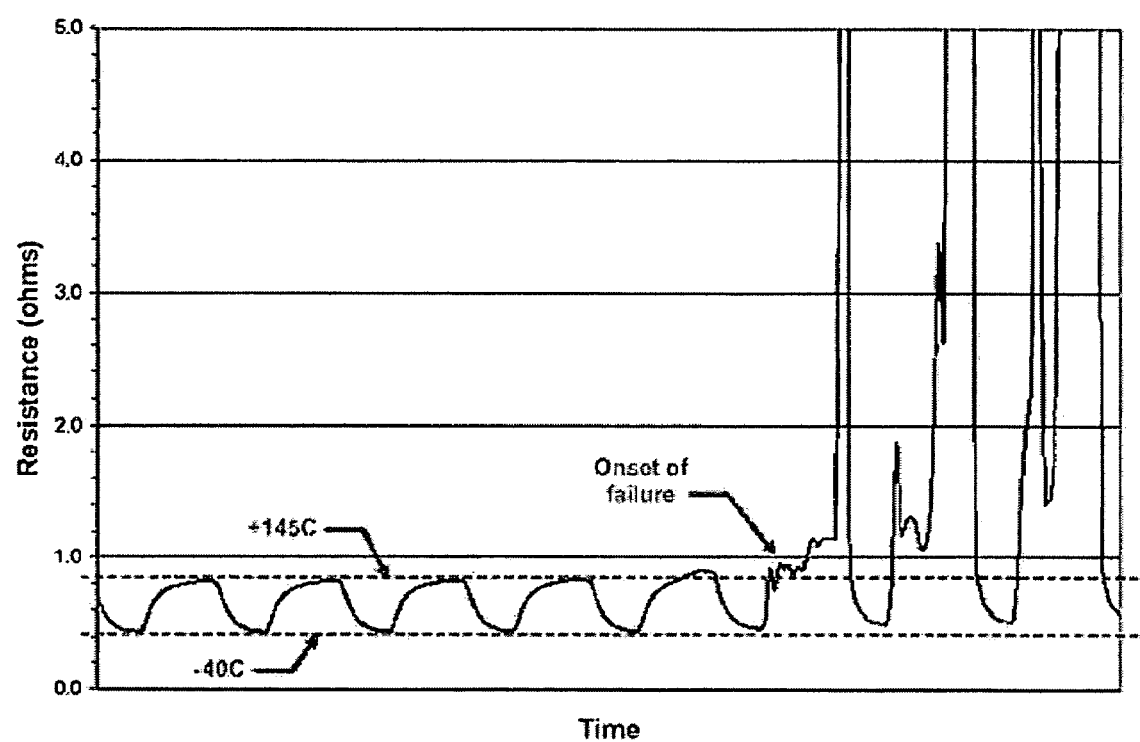
FIG. 4 shows the electrical resistance of one daisy-chain net in the DUT during thermal shock testing.

For this particular example, the temperature was required to be cycled from −40° C. to +145° C. An example resistance trace for a net is shown in FIG. 4. The graph shows the resistance varying from a low value to a high value corresponding to the thermal cycling. The sharp increase in resistance as component failure starts to occur is clearly depicted. It is therefore impossible to monitor the resistance of the samples as a method of determining their temperature once such failure is initiated. For this test it took the Thermal Shock system, with a cycle time of 60 minutes, over 41 days to complete 1000 cycles for all of the samples. The HATS system was able to provide cycle times in the range of 4-10 minutes, depending on coupon size, and was able to complete testing in 2.5-7 days.

Although the IST system completed the testing in a similar time frame, it had the disadvantages described above: its peak temperature went 25° C. higher that the required target temperature, which was problematic since 170° C. is greater than the glass transition temperature $T_g$ of certain components in the samples. In addition, the IST temperature range was only 145° C., much lower than the required 185° C., because its minimum temperature was only 25° C. Thus the samples were also not provided with low temperature exposure as required by the test parameters.

Although the invention has been described in detail with particular reference to these preferred embodiments, other embodiments can achieve the same results. Variations and modifications of the present invention will be obvious to those skilled in the art and it is intended to cover all such modifications and equivalents. The entire disclosures of all patents and publications cited above are hereby incorporated by reference.

What is claimed is:

1. An apparatus for thermal testing of one or more samples, said apparatus comprising:
   a single sample chamber;
   a cooler and a heater to vary a temperature of a fluid;
   a single opening in said chamber for introduction of said fluid; and
   a plurality of sample mounts for receiving the one or more samples circularly arranged around and equally distant from said opening;
   wherein the heated or cooled fluid contacts and thereby varies a temperature of the one or more samples; and
   wherein substantially no impediment to a flow of said fluid exists between any two adjacent samples.

2. The apparatus of claim 1 wherein the fluid temperature is lower than an ambient temperature.

3. The apparatus of claim 1 wherein the fluid temperature is higher than an ambient temperature.

4. The apparatus of claim 1 wherein said fluid comprises air.

5. The apparatus of claim 4 wherein said air is dried.

6. The apparatus of claim 5 wherein said air is compressed.

7. The apparatus of claim 1 wherein said fluid is cooled to a temperature lower than a desired low temperature.

8. The apparatus of claim 7 wherein said cooled fluid is subsequently heated to the desired low temperature.

9. The apparatus of claim 8 wherein said cooled fluid is subsequently heated to a desired high temperature.

10. The apparatus of claim 1 wherein said sample mounts are evenly spaced.

11. The apparatus of claim 1 wherein sufficient space exists between the one or more samples mounted in adjacent said sample mounts to permit uniform flow of said fluid.

12. The apparatus of claim 1 wherein said sample mounts comprise slots to receive the one or more samples.

13. The apparatus of claim 12 wherein said slots are oriented radially outward from said opening.

14. The apparatus of claim 1 wherein said fluid flows radially outward from said opening.

15. The apparatus of claim 1 wherein said sample mounts comprise electrical connectors.

16. The apparatus of claim 15 wherein said electrical connectors comprise an electronic switching network.

17. The apparatus of claim 16 wherein said network comprises at least one ohmmeter.

18. The apparatus of claim 17 wherein said network is in communication with a computer or processor.

19. The apparatus of claim 18 wherein said computer or processor comprises a data acquisition system.

20. The apparatus of claim 1 wherein the samples comprise test coupons.

21. The apparatus of claim 20 wherein the test coupons comprise at least one net.

22. The apparatus of claim 21 wherein the at least one net comprises a daisy-chain of vias.

23. A method for thermally testing one or more samples, the method comprising the steps of:
   circularly arranging one or more samples around and equally distant from a single opening in a single sample chamber;
   varying a temperature of a fluid using a cooler or a heater;
   introducing the fluid into the chamber via the single opening;
   contacting the samples with the fluid; and
   varying a temperature of the samples;
   wherein substantially no impediment to a flow of the fluid exists between any two adjacent samples.

24. The method of claim 23 wherein the fluid temperature is lower than an ambient temperature.

25. The method of claim 23 wherein the fluid temperature is higher than an ambient temperature.

26. The method of claim 23 wherein the fluid comprises air.

27. The method of claim 26 further comprising the step of drying the air.

28. The method of claim 26 further comprising the step of compressing the air.

29. The method of claim 23 wherein the step of varying the fluid temperature comprises cooling the fluid to a temperature lower than a desired low temperature.

30. The method of claim 29 further comprising the step of subsequently hearing the cooled fluid to the desired low temperature.

31. The method of claim 30 further comprising the step of subsequently heating the cooled fluid to a desired high temperature.

32. The method of claim 23 wherein the sample mounts are evenly spaced.

33. The method of claim 23 wherein sufficient space exists between the one or more samples mounted in adjacent said sample mounts to permit uniform flow of said fluid.

34. The method of claim 23 wherein said sample mounts comprise slots to receive the one or more samples.

35. The method of claim 23 wherein the slots are oriented radially outward from said opening.

36. The method of claim 23 further comprising the step of radially flowing the fluid outward from the opening.

* * * * *